United States Patent
Jandhyala et al.

(10) Patent No.: US 12,306,169 B2
(45) Date of Patent: May 20, 2025

(54) METHOD TO TAILOR CEMENT COMPOSITION TO WITHSTAND CARBON DIOXIDE INJECTION LOADS

(71) Applicant: Halliburton Energy Services, Inc., Houston, TX (US)

(72) Inventors: Siva Rama Krishna Jandhyala, The Woodlands, TX (US); Gunnar Lende, Stavanger (NO); Walmy Cuello Jimenez, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 141 days.

(21) Appl. No.: 17/840,100

(22) Filed: Jun. 14, 2022

(65) Prior Publication Data
US 2023/0400449 A1    Dec. 14, 2023

(51) Int. Cl.
*G01N 33/38* (2006.01)
*C04B 40/00* (2006.01)
*C09K 8/42* (2006.01)
*C04B 111/00* (2006.01)

(52) U.S. Cl.
CPC ....... *G01N 33/383* (2013.01); *C04B 40/0032* (2013.01); *C09K 8/42* (2013.01); *C04B 2111/00706* (2013.01); *C04B 2201/50* (2013.01)

(58) Field of Classification Search
CPC .............. G01N 33/383; C04B 40/0032; C04B 2111/00706; C04B 2201/50; C09K 8/42; G06F 16/24528; G06F 16/24553; G06Q 50/08; G06Q 50/10; G06Q 10/04; G06Q 50/26; B28B 11/245
See application file for complete search history.

(56) References Cited

U.S. PATENT DOCUMENTS

| | | | | |
|---|---|---|---|---|
| 2,942,458 A | * | 6/1960 | Kerr | G01N 3/48 73/82 |
| 6,029,521 A | * | 2/2000 | Lin | G01H 1/12 73/584 |
| 7,038,470 B1 | * | 5/2006 | Johnson | G01N 27/226 250/390.05 |
| 7,551,058 B1 | * | 6/2009 | Johnson | G01N 27/226 709/213 |

(Continued)

FOREIGN PATENT DOCUMENTS

KR    20200116709    4/2017

OTHER PUBLICATIONS

International Search Report and Written Opinion for International Patent Application No. PCT/US2023/010544 dated May 9, 2023.

(Continued)

*Primary Examiner* — Edwin J Toledo-Duran
(74) *Attorney, Agent, or Firm* — Thomas Rooney; C. Tumey Law Group PLLC

(57) ABSTRACT

Methods of the present disclosure relate to tailoring cement compositions to withstand carbon dioxide injection. A method comprises predicting a depth of carbonation in a cement sheath; predicting spatially varying mechanical properties of the cement composition due to the carbonation; and determining a mechanical response of the cement sheath based on the spatially varying mechanical properties of the cement composition.

18 Claims, 9 Drawing Sheets

(56) References Cited

U.S. PATENT DOCUMENTS

| | | | |
|---|---|---|---|
| 2012/0109611 A1* | 5/2012 | Loizzo | E21B 41/0064 703/10 |
| 2012/0206144 A1 | 8/2012 | Barlet-Gouedard | |
| 2013/0105160 A1 | 5/2013 | Khalfallah et al. | |
| 2014/0373755 A1* | 12/2014 | Forgeron | B28C 5/4203 106/638 |
| 2015/0168369 A1* | 6/2015 | Lee | G01N 23/207 436/133 |
| 2015/0232381 A1* | 8/2015 | Niven | B28C 7/024 106/709 |
| 2015/0309007 A1* | 10/2015 | Bellotti | G01N 29/348 73/597 |
| 2016/0107939 A1* | 4/2016 | Monkman | C04B 28/04 366/12 |
| 2017/0096874 A1 | 4/2017 | Parsons et al. | |
| 2017/0204718 A1* | 7/2017 | Pearl, Jr. | C09K 8/424 |
| 2017/0350872 A1* | 12/2017 | Heo | G06Q 50/10 |
| 2017/0370050 A1* | 12/2017 | Townsend | E01C 3/003 |
| 2018/0011077 A1* | 1/2018 | Ekinci | G01N 33/38 |
| 2020/0087207 A1* | 3/2020 | Shao | C04B 28/082 |
| 2020/0249204 A1 | 8/2020 | Jandhyala et al. | |
| 2021/0172280 A1 | 6/2021 | Singh et al. | |
| 2022/0388915 A1* | 12/2022 | Shao | B28B 11/243 |
| 2024/0076244 A1* | 3/2024 | Son | C04B 14/106 |

OTHER PUBLICATIONS

Jung et al. Probability-Based Concrete Carbonation Prediction Using On-Site Data. MDPI, Jun. 24, 2020, pp. 1-14. pp. 3, 6-12 and figures 4-5, 7.

Zhao, Xing-Hua et al. "The Effective Elastic Moduli of Concrete and Composite Materials." Composites Part B: Engineering Journal, vol. 29, Issue No. 1, 1998, pp. 31-40. PDF file. 10 pages.

Santra, Ashok et al. "Reaction of CO2 with Portland Cement at Downhole Conditions and the Role of Pozzolanic Supplements." Society of Petroleum Engineers SPE 121103 paper prepared for 2009 SPE International Symposium on Oilfield Chemistry, Apr. 2009, pp. 1-9. PDF file. 9 pages.

Han, Jiande et al. "Microstructure Modification of Carbonated Cement Paste with Six Kinds of Modern Microscopic Instruments." Journal of Materials in Civil Engineering, vol. 27, Issue No. 10, Oct. 2014, pp. 1-14. PDF file. 15 pages.

Chang, Cheng-Feng et al. "Strength and Elastic Modulus of Carbonated Concrete." American Concrete Institute Materials Journal, vol. 102, Issue No. 5, Sep. 2005, pp. 315-321. PDF file. 8 pages.

* cited by examiner

METHOD TO TAILOR CEMENT COMPOSITION TO WITHSTAND CARBON DIOXIDE INJECTION LOADS

BACKGROUND

During some oilfield operations, or for underground $CO_2$ storage, $CO_2$ is injected into a wellbore, resulting in a cement sheath being exposed to the $CO_2$, which in turn can alter chemical composition and mechanical properties of the cement sheath.

BRIEF DESCRIPTION OF THE DRAWINGS

These drawings illustrate certain aspects of some of the examples of the present disclosure and should not be used to limit or define the disclosure.

DETAILED DESCRIPTION

Figure 1:
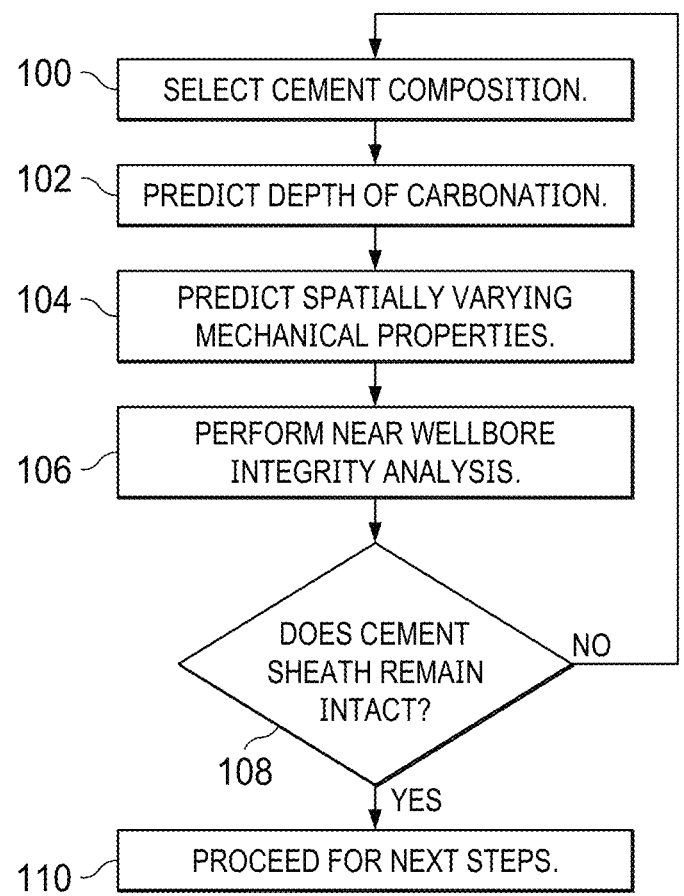
FIG. 1 illustrates a workflow for designing a cement composition for wells exposed to $CO_2$ injection, in accordance with examples of the present disclosure.

Methods of the present disclosure generally relate to tailoring (e.g., designing adjusting, and/or preparing) a cement composition to withstand exposure to $CO_2$ injection (s). Carbonation and bi-carbonation reactions alter (e.g., weaken) the mechanical properties of the cement. Such alterations occur only in the part of the cement that has been carbonated, with the rest of the uncarbonated portion(s) retaining the original mechanical properties of the cement. The cement in such a state is considered a composite (i.e., carbonated and uncarbonated portions) that evolves with time. Carbonated portion evolves (increases) with time. Further, mechanical properties at a point in space also evolve with time because CSH reaction with $CO_2$ is a kinetic process. The $CO_2$ causes spatial variations in the mechanical properties in the composite. The spatial variations are used to assess the ability of a cement sheath to offer zonal isolation after being exposed to the $CO_2$ injection.

A mechanical response of the cement sheath to wellbore loads due to the $CO_2$ injection are analyzed, which allows for development of a cement composition that provides long term (e.g., life of the well) zonal isolation. The extent of the carbonation reaction(s) is determined. Then, the mechanical properties as well as volumetric expansion for the carbonated zone are determined separately from the uncarbonated zone. Those properties are then used in near wellbore integrity analysis (e.g., via software) to determine the mechanical response of the cement. Optionally changes in permeability can be included.

In some examples, a cement composition is selected. Then, depth of carbonation for a desired time of exposure is predicted. A model used for prediction can directly relate depth of penetration with PSD (e.g., $D_{50}$), composition, porosity (water/solids volume) and exposure conditions. Alternatively, the depth of carbonation can be related to permeability and exposure conditions. Permeability in turn will be a function of particle size distribution (PSD), porosity (water/solids volume) and chemical composition.

After predicting the depth of carbonation, the mechanical properties of the carbonated and uncarbonated portion are predicted. A hardness test can be performed on a carbonated portion of a cement sample which may be recovered from $CO_2$ exposure experiments. The measured indentation values from the hardness test can be used in 'Hardness-Strength' calibration curves to predict compressive strength and tensile strength. Elastic properties scale with porosity; therefore, Young's modulus (YM) and Poisson's ratio (PR) are obtained using a combination of porosity measurements along with 'elastic properties-porosity' calibration curves. Alternatively, velocities of s and p waves can be used to determine (dynamic) YM and PR for carbonated and uncarbonated zones separately. Carbonation can result in volumetric expansion. This will affect the stress state of the cement sheath. Expansion measurements of unexposed and $CO_2$ exposed samples with a known extent of carbonation can be used to determine the additional expansion because of the carbonation process.

After predicting the mechanical properties of the carbonated and uncarbonated portion, a near wellbore integrity analysis is performed to assess the mechanical response of the composite cement. In this analysis, anticipated pressure and temperature loads are applied on a wellbore model, along with any volumetric expansion loads from the carbonation process. Response of the wellbore model is quantified in the form of stresses, temperatures and deformations in cement and other wellbore materials. In accordance with spatial variation of properties, the results (e.g., stresses) also vary in space. For example, carbonated portions of cement can have higher stresses and stress gradients than the uncarbonated portion. This is due to the deposition of calcite, which results in an increase in stiffness and a reduction in porosity, which affects the bulk modulus (compressibility). Comparison of stresses with strength of cement predicted from the second step will help determine the risk of failure, either in carbonated or uncarbonated portion of the matrix or at their boundary. If no risk of failure is shown, the selected cement composition can be considered suitable for use. Otherwise, an alternate cement composition is selected, and the above-mentioned steps may be repeated until the point of successfully identifying cement composition(s) that can withstand loads exerted by the wellbore.

Figure 2:
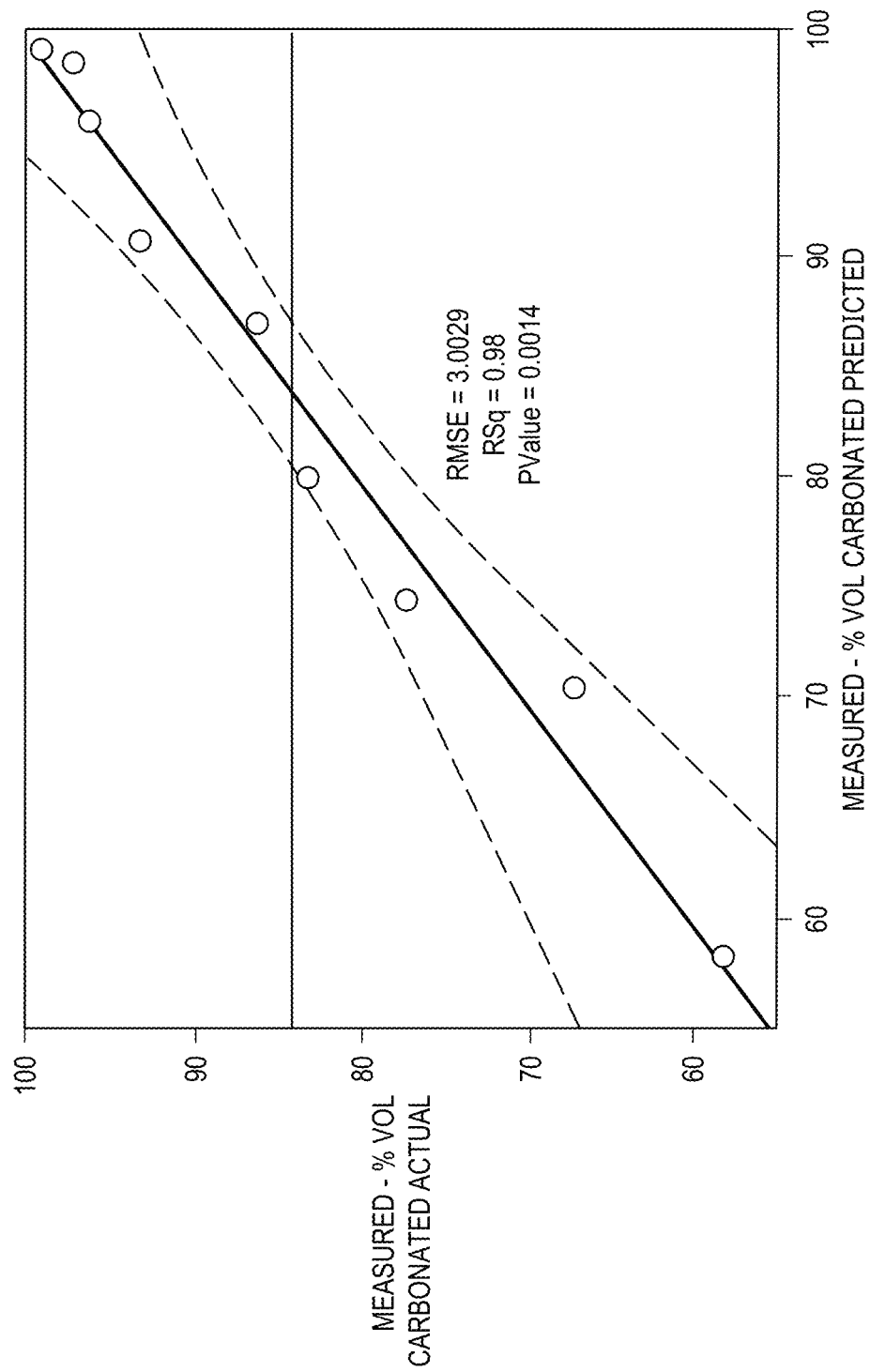
FIG. 2 illustrates a graph of predicted depth of penetration versus % volume carbonated, for a series of compositions, in accordance with examples of the present disclosure.

FIG. 1 illustrates a method for designing a cement composition to withstand $CO_2$ injection, in accordance with examples of the present disclosure. At box 100, a cement composition is selected. At box 102, a depth of carbonation is determined. For example, the predicted depth of penetration vs. measured value (expressed as % vol carbonated) is shown for a series of compositions in FIG. 2. These nine compositions comprise of Portland, fly ash (FA) and silica fume (SF) in varying amounts, resulting in different density for each design. The cured compositions in FIG. 2 are exposed to super critical $CO_2$ (e.g., at 2000 psi and 200° F. for 15 days). Test conditions and exposure duration can be tailored to the particular application. After exposure, the depth of carbonation is measured.

The model used to predict depth of carbonation in FIG. 2 directly related depth of penetration with PSD (e.g., $D_{50}$), composition and water/solids volume via Equation 1.

$$\% \, vol \, \text{carbonation} = k_1 + k_2 \frac{\text{water } vol}{\text{solids } vol} + k_3 D_{50} + k_4 \% FA + k_5 \% SF \quad \text{Eq. (1)}$$

$k_1$-$k_4$ are model parameters that characterize the role of each variable on depth of penetration. These values can be different for different materials or material type. For example, $k_4$ being different than $k_5$ indicate that the role of fly ash in controlling depth of penetration is different from the role of silica fume. This brings in the design element into the process.

Exposure conditions are not included because all compositions have been subjected to the same exposure conditions. Instead of relating to individual parameters as in Equation 1, the depth of carbonation can be related to permeability and exposure conditions. Permeability in turn will be a function of particle size distribution (PSD), porosity (water/solids volume) and chemical composition.

Equation 1 is a non-limiting example. Alternate forms of equations such as power law, exponential, transcendental may also be used. Data driven black box models like neural nets, decision trees may also be used to relate depth of penetration to composition and exposure conditions. Further, depth of carbonation may be related to permeability or to each independent parameter as in Equation 1. Generic equation forms may include Equations 2 and 3, or Equation 4:

$$\text{depth of carbonation} = f(\text{permeability}, T, P, \text{time, state of } CO_2) \quad \text{Eq. (2)}$$

$$\text{permeability} = f\left(\frac{\text{water } vol}{\text{solids } vol}, PSD, \text{composition}\right) \quad \text{Eq. (3)}$$

$$\text{depth of carbonation} = \quad \text{Eq. (4)}$$
$$f\left(\frac{\text{water } vol}{\text{solids } vol}, PSD, \text{composition}, T, P, \text{time, state of } CO_2\right)$$

At box 104, mechanical properties of the carbonated and uncarbonated portions are predicted. Depth of carbonation is used to identify boundary between carbonated and uncarbonated zones. Having known the boundary, measurements of hardness or sonic waves are taken in the carbonated portion only and processed to obtain mechanical properties of the carbonated portion. The same is repeated for the uncarbonated portion.

Mechanical properties include compressive strength, tensile strength, Young's modulus, and/or Poisson's ratio. In some examples, the mechanical properties of the uncarbonated portion can be the same as the original values if the initial curing is sufficient to ensure almost complete hydration. mechanical properties of carbonated portion are obtained. The original values are for a cement composition that is cured and subjected to mechanical properties testing without exposing it to $CO_2$. This allows for the use of techniques like static compressive strength and YM using extensometers and load frame, for example.

For compressive and tensile strength of the carbonated portions, the following procedure can be adopted. A hardness test can be performed on the carbonated portion of the sample. Depth of carbonation draws the boundary within which the measurements are taken, to confirm measurements are exclusive to either the carbonated or the uncarbonated zone.

Figure 3:
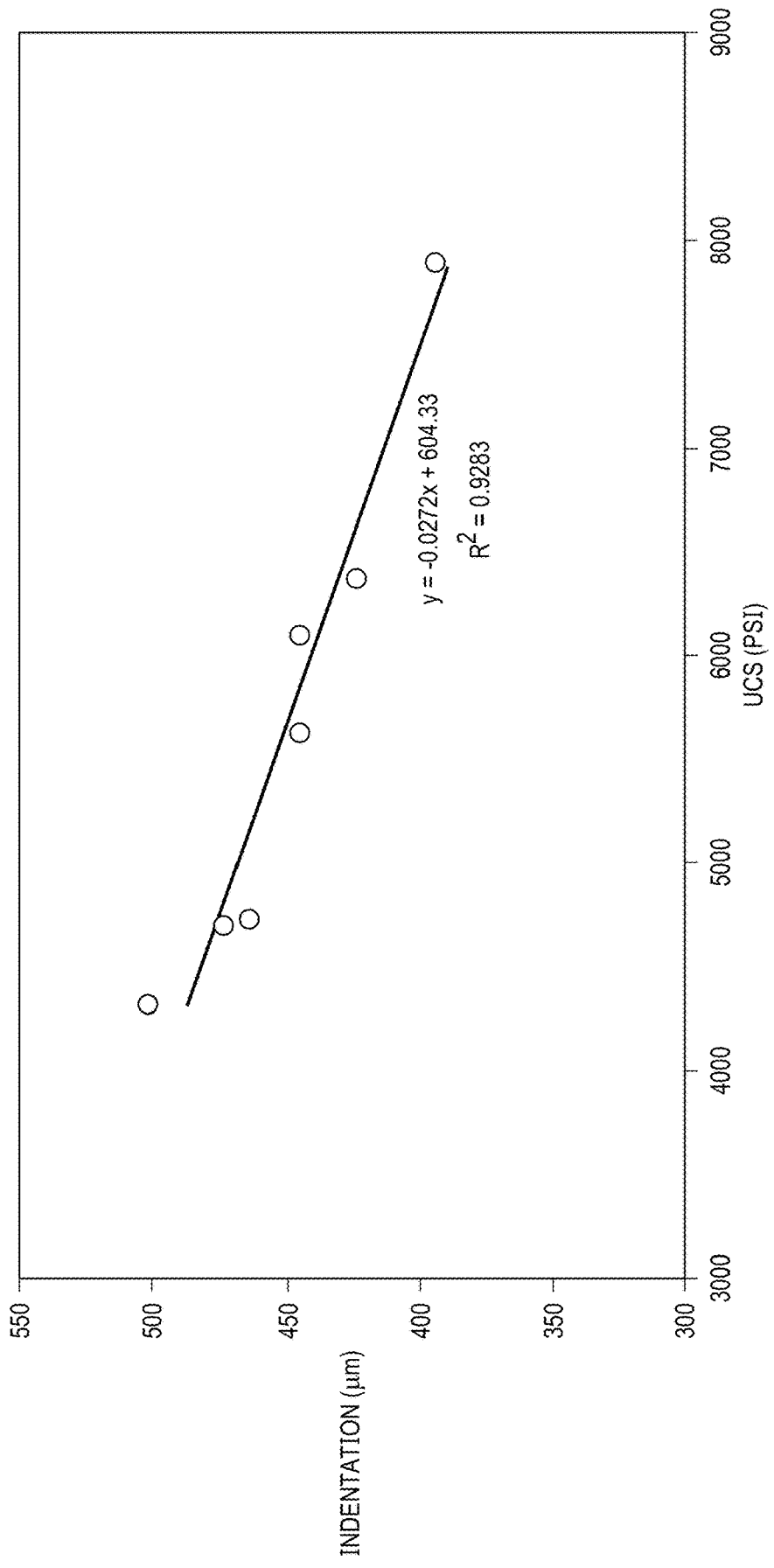
FIG. 3 illustrates a calibration curve relating indentation values to compressive strengths for some cement compositions, in accordance with examples of the present disclosure.

For hardness, a predetermined indentation level can be set, and the force required to reach this indentation level can be recorded. The measured force can be used in a calibration curve to predict compressive strength. Alternately, the measured indentation values from the hardness test at a predetermined force value can be used in a calibration curve to predict compressive strength. For example, FIG. 3 shows a calibration curve relating indentation values to compressive strengths for few cement compositions. Similar calibration curves can be extracted for indentation depth vs. tensile strength.

Figure 4:
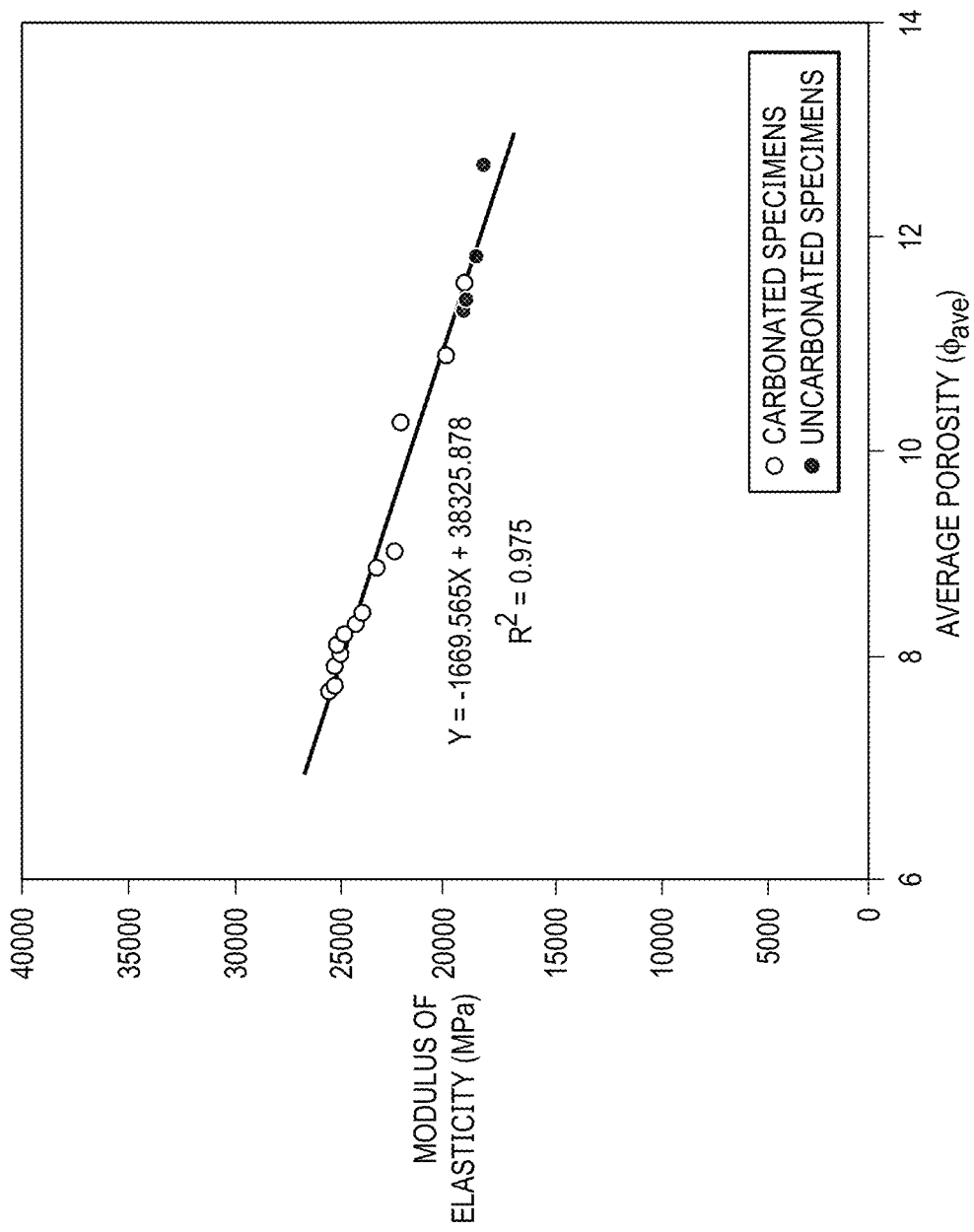
FIG. 4 illustrates poro-mechanical relationships exist to deduce YM and PR using wave velocities, in accordance with examples of the present disclosure.

Young's modulus (YM) and Poisson's ratio (PR) can be obtained using one of two approaches. The first approach uses s and p wave velocity measurements through the carbonated portion. Standard poro-mechanical relationships exist to deduce YM and PR using wave velocities. In the second approach, YM and PR can be related to porosity of carbonated portion. FIG. 4 shows an example of such relation for YM. Alternatively, nanoindentation testing targeting the specific cement phases (i.e., carbonated, non-carbonated) can be used to measure mechanical properties. When using the second approach, it is necessary to measure porosity of the composite sample. If porosity of the unexposed sample and the depth of penetration are known, it is possible to calculate the porosity of carbonated portion by utilizing the composite sample's porosity. That porosity can be used in a calibration curve on FIG. 4, to predict YM and PR of the carbonated portion. Volumetric expansion (e.g., radial and/or circumferential expansion) due to carbonation can be determined using annular ring test or any other custom measurement of sample dimension with time.

At box 106, a near wellbore integrity analysis is performed to assess the mechanical response of the composite cement. A typical stress result from such analysis is shown in FIG. 5.

Figure 5:
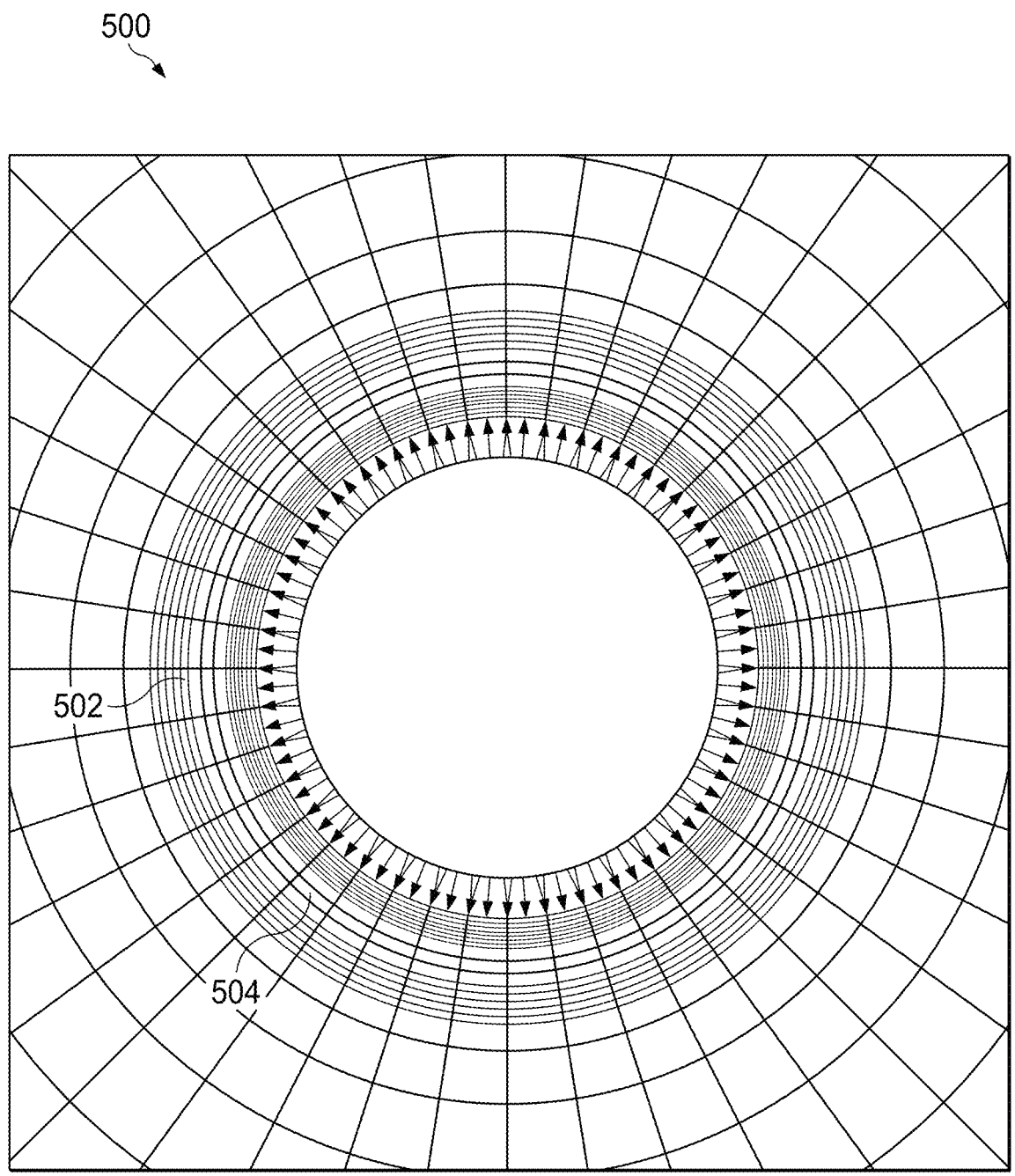
FIG. 5 illustrates a mesh of a finite element model used to predict a response of a composite cement sheath, in accordance with examples of the present disclosure.

FIG. 5 shows a mesh of the finite element model used to predict response of composite cement sheath 500. An outer portion 502 is a carbonated portion of the cement sheath 500, and the inner portion 504 is an uncarbonated portion of the cement sheath 500. These two portions have different mechanical properties. Specifically, the outer portion 502 is stiffer than the inner portion 504 due to deposition of calcite in pore space, increasing the stiffness. The degree of carbonation both radially and axially may be determined. In some examples, carbonated and uncarbonated portions of annular sealants as well as abandonment plugs may be analyzed according to the techniques described herein.

Figure 6:
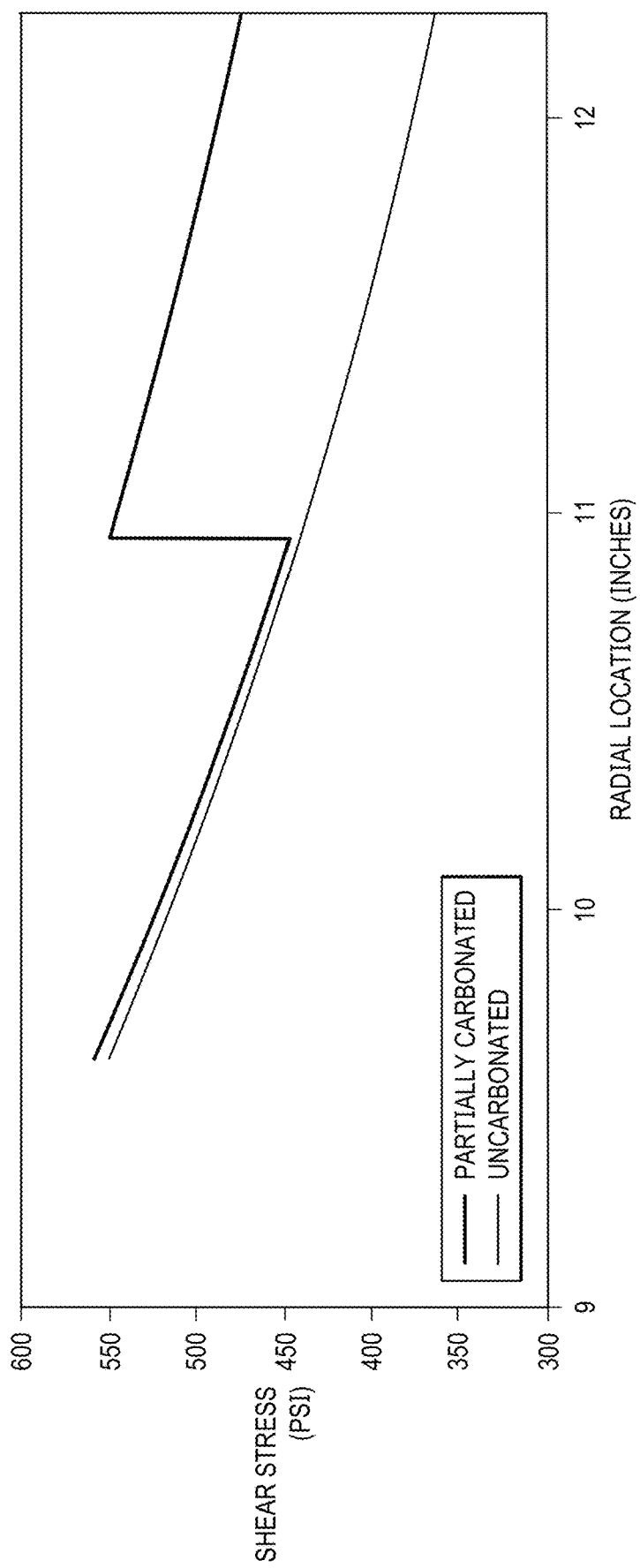
FIG. 6 illustrates shear stress and radial location for carbonated and uncarbonated portion of cement, in accordance with examples of the present disclosure.
Figure 7:
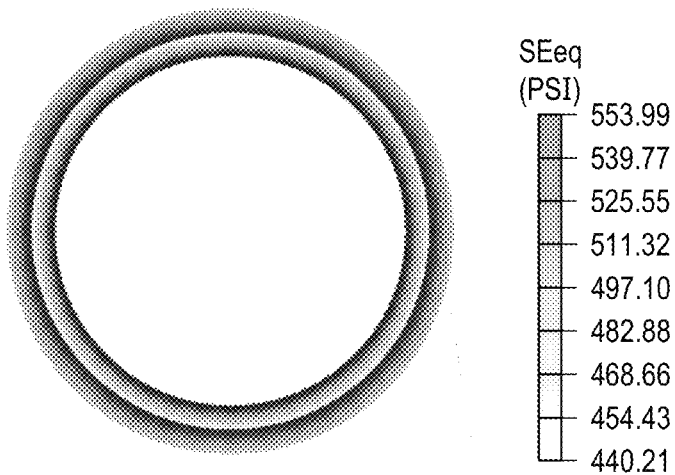
FIG. 7 illustrates a contour plot of shear stresses in a cement sheath where the boundary between carbonated and uncarbonated zones is visible in the form of a rapid change in stresses.

In accordance with spatial variation of properties, the stress results also vary in space as shown on FIG. 6. FIG. 6 shows radial variation of shear stress in cement portion only. For example, cement inner diameter is 9.625" and outer diameter is 12.2". Shear stress can be compared to shear (i.e., compressive) strength to indicate risk of failure under compression. Like shear stress, graphs of radial stress and axial stress can be plotted as a function of radius. A jump in shear stress at about 10.8" is the boundary between the inner uncarbonated portion and the outer carbonated portion. FIG. 7 shows shear stress as a contour plot in the entire space of cement, clearly indicating sudden stress changes at the edge of two portions of cement.

For example, outer portion of partially carbonated cement has higher stress than the uncarbonated cement. This is because of the deposition of calcite. Stresses form analysis of the kind shown in FIG. 5 can be compared to failure properties of respective portions to determine if there is a risk of failure in cement sheath (i.e., cement sheath remains intact), at box 108. Compressive strength and tensile strength are the failure properties. If there is not any risk of failure or if the risk of failure is below an acceptable threshold, the cement composition selected at box 100 can be considered as fit for use (e.g., production) at box 110. Otherwise, an alternate cement composition should be picked at box 100 until the point of successfully identifying cement composition(s) that can withstand $CO_2$ injection. Risk can be quantified using a derived variable "stress exerted/strength." A value greater than zero indicates that the material (cement sheath) did not fail. In some examples, there may be a need for a safety factor that may depend upon the particular scenario.

For example, if the cement sheath experiences cyclic loading, a stress exerted/strength less than or equal to 0.6 may be considered low risk. The safety factor value here is 0.6 and comes from cyclic testing experiments that indicate low risk of fatigue damage in cement when loading cyclically below 60% of the strength. If there is no cyclic loading, the safety factor should only account for uncertainty in quality of inputs (e.g., geometry, loads).

Figure 8:
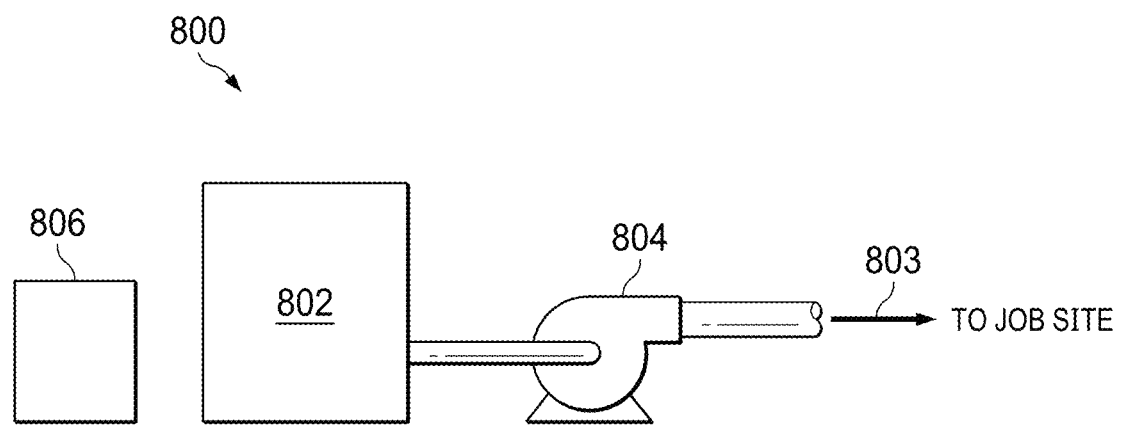
FIG. 8 illustrates a system for the preparation of a designed composition and subsequent delivery of the composition to an application site, in accordance with examples of the present disclosure.

FIG. 8 illustrates a system 800 for the preparation of a designed cement composition and subsequent delivery of the composition to an application site, in accordance with examples of the present disclosure. As shown, components may be mixed and/or stored in a vessel 802. The vessel 802 may be configured to contain and/or mix the components to produce or modify a designed composition 803 (e.g., a fluid, a cement). Non-limiting examples of the vessel 802 may include drums, barrels, tubs, bins, jet mixers, re-circulating mixers, and/or batch mixers. The designed composition 803 may then be moved (e.g., pumped via pumping equipment 804) to a location.

The system 800 may also include a computer 806 for performing the workflow of FIG. 1 and to prepare the designed composition. The computer 806 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. The computer 806 may be any processor-driven device, such as, but not limited to, a personal computer, laptop computer, smartphone, tablet, handheld computer, dedicated processing device, and/or an array of computing devices. In addition to having a processor, the computer 806 may include a server, a memory, input/output ("I/O") interface(s), and a network interface. The memory may be any computer-readable medium, coupled to the processor, such as RAM, ROM, and/or a removable storage device for storing data and a database management system ("DBMS") to facilitate management of data stored in memory and/or stored in separate databases.

The computer 806 may also include display devices such as a monitor featuring an operating system, media browser, and the ability to run one or more software applications. Additionally, the computer 806 may include non-transitory computer-readable media. Non-transitory computer-readable media may include any instrumentality or aggregation of instrumentalities that may retain data and/or instructions for a period of time.

Figure 9:
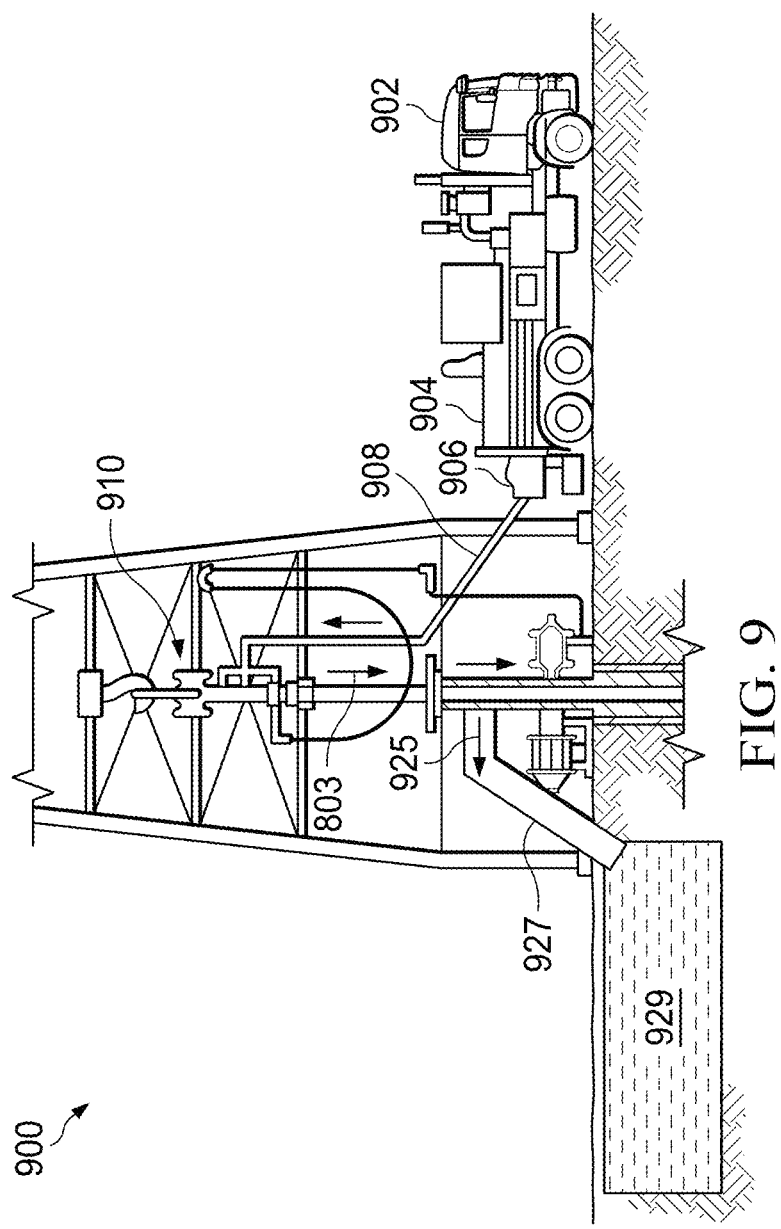
FIG. 9 illustrates a system that may be used in the placement of a cement composition, in accordance with examples of the present disclosure.

FIG. 9 illustrates a system 900 that may be used in the placement of a designed composition, in accordance with examples of the present disclosure. It should be noted that while FIG. 9 generally depicts a land-based operation, those skilled in the art will readily recognize that the principles described herein are equally applicable to subsea operations that employ floating or sea-based platforms and rigs, without departing from the scope of the disclosure.

The system 900 may include a cementing unit 902, which may include one or more cement trucks, for example. The cementing unit 902 may include mixing equipment 904 and pumping equipment 906. The cementing unit 902 may pump the designed composition 803, through a feed pipe 908 and to a cementing head 910 which conveys the composition 803 into a downhole environment.

Figure 10:
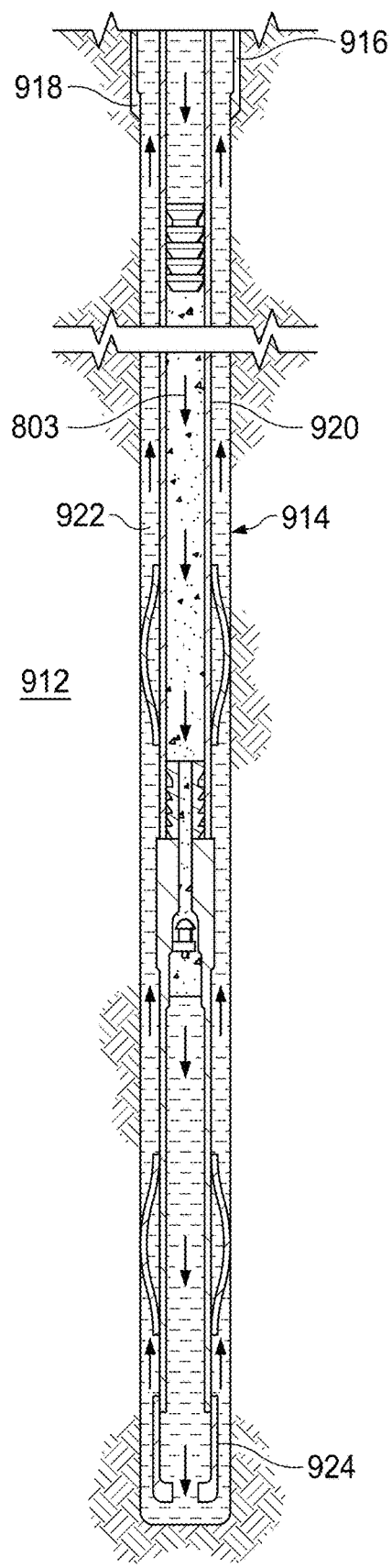
FIG. 10 illustrates the cement composition placed into a subterranean formation, in accordance with particular examples of the present disclosure.

With additional reference to FIG. 10, the composition 803 may be placed in a subterranean formation 912. A wellbore 914 may be drilled into the subterranean formation 912. While the wellbore 914 is shown generally extending vertically into the subterranean formation 912, the principles described herein are also applicable to wellbores that extend at an angle through subterranean formation 912, such as horizontal and slanted wellbores.

A first section 916 of casing may be inserted into the wellbore 914. The section 916 may be cemented in place by a cement sheath 918. A second section 920 of casing may also be disposed in the wellbore 914. A wellbore annulus 922 formed between the second section 920 and walls of the wellbore 914 and/or the first section 916.

The composition 803 may be pumped down the interior of the second section 920 of casing. The composition 803 may be allowed to flow down the interior of the casing through the casing shoe 924 at the bottom of the second section 920 and up around the second section 920 of casing into the wellbore annulus 922. As it is introduced, the composition 803 may displace other fluids 925, such as drilling fluids and/or spacer fluids that may be present in the interior of the casing and/or the wellbore annulus 922. At least a portion of the displaced fluids 925 may exit the wellbore annulus 922 via a flow line 927 and be deposited, for example, in one or more retention pits 929.

Other techniques may also be utilized for introduction of the composition 803. For example, reverse circulation techniques may be used that include introducing the composition 803 into the subterranean formation 912 via the wellbore annulus 922 instead of through the casing (e.g., section 920).

Cement slurries described herein may generally include a hydraulic cement and water. A variety of hydraulic cements may be utilized in accordance with the present disclosure, including, but not limited to, those comprising calcium, aluminum, silicon, oxygen, iron, and/or sulfur, which set and harden by reaction with water. Suitable hydraulic cements may include, but are not limited to, Portland cements, pozzolana cements, gypsum cements, high alumina content cements, silica cements, and any combination thereof. In certain examples, the hydraulic cement may include a Portland cement. In some examples, the Portland cements may include Portland cements that are classified as Classes A, C, H, and G cements according to American Petroleum Institute, *API Specification for Materials and Testing for Well Cements*, API Specification 10, Fifth Ed., Jul. 1, 1990. In addition, hydraulic cements may include cements classified by American Society for Testing and Materials (ASTM) in C150 (Standard Specification for Portland Cement), C595 (Standard Specification for Blended Hydraulic Cement) or C1157 (Performance Specification for Hydraulic Cements) such as those cements classified as ASTM Type I, II, or III. The hydraulic cement may be included in the cement slurry in any amount suitable for a particular composition. Without limitation, the hydraulic cement may be included in the cement slurries in an amount in the range of from about 10% to about 80% by weight of dry blend in the cement slurry. For example, the hydraulic cement may be present in an amount ranging between any of and/or including any of about 10%, about 15%, about 20%, about 25%, about 30%, about 35%, about 40%, about 45%, about 50%, about 55%, about 60%, about 65%, about 70%, about 75%, or about 80% by weight of the cement slurries.

The water may be from any source provided that it does not contain an excess of compounds that may undesirably affect other components in the cement slurries. For example, a cement slurry may include fresh water or saltwater. Saltwater generally may include one or more dissolved salts therein and may be saturated or unsaturated as desired for a particular application. Seawater or brines may be suitable for use in some examples. Further, the water may be present in an amount sufficient to form a pumpable slurry. In certain examples, the water may be present in the cement slurry in an amount in the range of from about 33% to about 200% by weight of the cementitious materials. For example, the water cement may be present in an amount ranging between any of and/or including any of about 33%, about 50%, about 75%, about 100%, about 125%, about 150%, about 175%, or about 200% by weight of the cementitious materials. The cementitious materials referenced may include all components which contribute to the compressive strength of the cement slurry such as the hydraulic cement and supplementary cementitious materials, for example.

As mentioned above, the cement slurry may include supplementary cementitious materials. The supplementary cementitious material may be any material that contributes to the desired properties of the cement slurry. Some supplementary cementitious materials may include, without limitation, fly ash, blast furnace slag, silica fume, pozzolans, kiln dust, and clays, for example.

The cement slurry may include kiln dust as a supplementary cementitious material. "Kiln dust," as that term is used herein, refers to a solid material generated as a by-product of the heating of certain materials in kilns. The term "kiln dust" as used herein is intended to include kiln dust made as described herein and equivalent forms of kiln dust. Depending on its source, kiln dust may exhibit cementitious properties in that it can set and harden in the presence of water. Examples of suitable kiln dusts include cement kiln dust, lime kiln dust, and combinations thereof. Cement kiln dust may be generated as a by-product of cement production that is removed from the gas stream and collected, for example, in a dust collector. Usually, large quantities of cement kiln dust are collected in the production of cement that are commonly disposed of as waste. The chemical analysis of the cement kiln dust from various cement manufactures varies depending on a number of factors, including the particular kiln feed, the efficiencies of the cement production operation, and the associated dust collection systems. Cement kiln dust generally may include a variety of oxides, such as $SiO_2$, $Al_2O_3$, $Fe_2O_3$, CaO, MgO, $SO_3$, $Na_2O$, and $K_2O$. The chemical analysis of lime kiln dust from various lime manufacturers varies depending on several factors, including the particular limestone or dolomitic limestone feed, the type of kiln, the mode of operation of the kiln, the efficiencies of the lime production operation, and the associated dust collection systems. Lime kiln dust generally may include varying amounts of free lime and free magnesium, limestone, and/or dolomitic limestone and a variety of oxides, such as $SiO_2$, $Al_2O_3$, $Fe_2O_3$, CaO, MgO, $SO_3$, $Na_2O$, and $K_2O$, and other components, such as chlorides. A cement kiln dust may be added to the cement slurry prior to, concurrently with, or after activation. Cement kiln dust may include a partially calcined kiln feed which is removed from the gas stream and collected in a dust collector during the manufacture of cement. The chemical analysis of CKD from various cement manufactures varies depending on a number of factors, including the particular kiln feed, the efficiencies of the cement production operation, and the associated dust collection systems. CKD generally may comprise a variety of oxides, such as $SiO_2$, $Al_2O_3$, $Fe_2O_3$, CaO, MgO, $SO_3$, $Na_2O$, and $K_2O$. The CKD and/or lime kiln dust may be included in examples of the cement slurry in an amount suitable for a particular application.

In some examples, the cement slurry may further include one or more of slag, natural glass, shale, amorphous silica, or metakaolin as a supplementary cementitious material. Slag is generally a granulated, blast furnace by-product from the production of cast iron including the oxidized impurities found in iron ore. The cement may further include shale. A variety of shales may be suitable, including those including silicon, aluminum, calcium, and/or magnesium. Examples of suitable shales include vitrified shale and/or calcined shale. In some examples, the cement slurry may further include amorphous silica as a supplementary cementitious material. Amorphous silica is a powder that may be included in embodiments to increase cement compressive strength. Amorphous silica is generally a byproduct of a ferrosilicon production process, wherein the amorphous silica may be formed by oxidation and condensation of gaseous silicon suboxide, SiO, which is formed as an intermediate during the process In some examples, the cement slurry may further include a variety of fly ashes as a supplementary cementitious material which may include fly ash classified as Class C, Class F, or Class N fly ash according to American Petroleum Institute, API Specification for Materials and Testing for Well Cements, API Specification 10, Fifth Ed., Jul. 1, 1990. In some examples, the cement slurry may further include zeolites as supplementary cementitious materials. Zeolites are generally porous alumino-silicate minerals that may be either natural or synthetic. Synthetic zeolites are based on the same type of structural cell as natural zeolites and may comprise aluminosilicate hydrates. As used herein, the term "zeolite" refers to all natural and synthetic forms of zeolite.

Where used, one or more of the aforementioned supplementary cementitious materials may be present in the cement slurry. For example, without limitation, one or more supplementary cementitious materials may be present in an amount of about 0.1% to about 80% by weight of the cement slurry. For example, the supplementary cementitious materials may be present in an amount ranging between any of and/or including any of about 0.1%, about 10%, about 20%, about 30%, about 40%, about 50%, about 60%, about 70%, or about 80% by weight of the cement.

In some examples, the cement slurry may further include hydrated lime. As used herein, the term "hydrated lime" will be understood to mean calcium hydroxide. In some embodiments, the hydrated lime may be provided as quicklime (calcium oxide) which hydrates when mixed with water to form the hydrated lime. The hydrated lime may be included in examples of the cement slurry, for example, to form a hydraulic composition with the supplementary cementitious components. For example, the hydrated lime may be included in a supplementary cementitious material-to-hydrated-lime weight ratio of about 10:1 to about 1:1 or 3:1 to about 5:1. Where present, the hydrated lime may be included in the set cement slurry in an amount in the range of from about 10% to about 100% by weight of the cement slurry, for example. In some examples, the hydrated lime may be present in an amount ranging between any of and/or including any of about 10%, about 20%, about 40%, about 60%, about 80%, or about 100% by weight of the cement slurry. In some examples, the cementitious components present in the cement slurry may consist essentially of one or more supplementary cementitious materials and the hydrated lime. For example, the cementitious components may primarily comprise the supplementary cementitious materials and the hydrated lime without any additional components (e.g., Portland cement, fly ash, slag cement) that hydraulically set in the presence of water.

Lime may be present in the cement slurry in several; forms, including as calcium oxide and or calcium hydroxide or as a reaction product such as when Portland cement reacts with water. Alternatively, lime may be included in the cement slurry by amount of silica in the cement slurry. A cement slurry may be designed to have a target lime to silica weight ratio. The target lime to silica ratio may be a molar ratio, molal ratio, or any other equivalent way of expressing a relative amount of silica to lime. Any suitable target time to silica weight ratio may be selected including from about 10/90 lime to silica by weight to about 40/60 lime to silica by weight. Alternatively, about 10/90 lime to silica by weight to about 20/80 lime to silica by weight, about lime to silica by weight to about 30/70 lime to silica by weight, or about 30/70 lime to silica by weight to about 40/63 lime to silica by weight.

Other additives suitable for use in subterranean cementing operations also may be included in embodiments of the cement slurry. Examples of such additives include, but are not limited to weighting agents, lightweight additives, gas-generating additives, mechanical-property-enhancing additives, lost-circulation materials, filtration-control additives, fluid-loss-control additives, defoaming agents, foaming agents, thixotropic additives, and combinations thereof. In embodiments, one or more of these additives may be added to the cement slurry after storing but prior to the placement of a cement slurry into a subterranean formation. In some examples, the cement slurry may further include a dispersant. Examples of suitable dispersants include, without limitation, sulfonated-formaldehyde-based dispersants (e.g., sulfonated acetone formaldehyde condensate) or polycarboxylated ether dispersants. In some examples, the dispersant may be included in the cement slurry in an amount in the range of from about 0.01% to about 5% by weight of the cementitious materials. In specific examples, the dispersant may be present in an amount ranging between any of and/or including any of about 0.01%, about 0.1%, about 0.5%, about 1%, about 2%, about 3%, about 4%, or about 5% by weight of the cementitious materials.

In some examples, the cement slurry may further include a set retarder. A broad variety of set retarders may be suitable for use in the cement slurries. For example, the set retarder may comprise phosphonic acids, such as ethylenediamine tetra(methylene phosphonic acid), diethylenetriamine penta (methylene phosphonic acid), etc.; lignosulfonates, such as sodium lignosulfonate, calcium lignosulfonate, etc.; salts such as stannous sulfate, lead acetate, monobasic calcium phosphate, organic acids, such as citric acid, tartaric acid, etc.; cellulose derivatives such as hydroxyl ethyl cellulose (HEC) and carboxymethyl hydroxyethyl cellulose (CMHEC); synthetic co- or ter-polymers comprising sulfonate and carboxylic acid groups such as sulfonate-functionalized acrylamide-acrylic acid co-polymers; borate compounds such as alkali borates, sodium metaborate, sodium tetraborate, potassium pentaborate; derivatives thereof, or mixtures thereof. Examples of suitable set retarders include, among others, phosphonic acid derivatives. Generally, the set retarder may be present in the cement slurry in an amount sufficient to delay the setting for a desired time. In some examples, the set retarder may be present in the cement slurry in an amount in the range of from about 0.01% to about 10% by weight of the cementitious materials. In specific examples, the set retarder may be present in an amount ranging between any of and/or including any of about 0.01%, about 0.1%, about 1%, about 2%, about 4%, about 6%, about 8%, or about 10% by weight of the cementitious materials.

In some examples, the cement slurry may further include an accelerator. A broad variety of accelerators may be suitable for use in the cement slurries. For example, the accelerator may include, but are not limited to, aluminum sulfate, alums, calcium chloride, calcium nitrate, calcium nitrite, calcium formate, calcium sulphoaluminate, calcium sulfate, gypsum-hemihydrate, sodium aluminate, sodium carbonate, sodium chloride, sodium silicate, sodium sulfate, ferric chloride, or a combination thereof. In some examples, the accelerators may be present in the cement slurry in an amount in the range of from about 0.01% to about 10% by weight of the cementitious materials. In specific examples, the accelerators may be present in an amount ranging between any of and/or including any of about 0.01%, about 0.1%, about 1%, about 2%, about 4%, about 6%, about 8%, or about 10% by weight of the cementitious materials.

Cement slurries generally should have a density suitable for a particular application. By way of example, the cement slurry may have a density in the range of from about 8 pounds per gallon ("ppg") (959 kg/m$^3$) to about 20 ppg (2397 kg/m$^3$), or about 8 ppg to about 12 ppg (1437. Kg/m$^3$), or about 12 ppg to about 16 ppg (1917.22 kg/m$^3$), or about 16 ppg to about 20 ppg, or any ranges therebetween. Examples of the cement slurry may be foamed or unfoamed or may comprise other means to reduce their densities, such as hollow microspheres, low-density elastic beads, or other density-reducing additives known in the art.

The cement slurries disclosed herein may be used in a variety of subterranean applications, including primary and remedial cementing. The cement slurries may be introduced into a subterranean formation and allowed to set. In primary cementing applications, for example, the cement slurries may be introduced into the annular space between a conduit located in a wellbore and the walls of the wellbore (and/or a larger conduit in the wellbore), wherein the wellbore penetrates the subterranean formation. The cement slurry may be allowed to set in the annular space to form an annular sheath of hardened cement. The cement slurry may form a barrier that prevents the migration of fluids in the wellbore. The cement slurry may also, for example, support the conduit in the wellbore. In remedial cementing applications, the cement slurry may be used, for example, in squeeze cementing operations or in the placement of cement plugs. By way of example, the cement slurry may be placed in a wellbore to plug an opening (e.g., a void or crack) in the formation, in a gravel pack, in the conduit, in the cement sheath, and/or between the cement sheath and the conduit (e.g., a micro annulus).

Accordingly, the methods of the present disclosure analyze suitability of a cement compositions for use in wells that may experience $CO_2$ injections. The methods may include any of the various features disclosed herein, including one or more of the following statements.

Statement 1. A method comprises predicting a depth of carbonation in a cement sheath formed from a cement composition; predicting spatially varying mechanical properties of the cement composition due to the carbonation; and determining a mechanical response of the cement sheath based on the spatially varying mechanical properties of the cement composition.

Statement 2. The method of the statement 1, further comprising preparing the cement composition based on the mechanical response of the cement sheath.

Statement 3. The method of any of the preceding statements, wherein the step of predicting spatially varying mechanical properties due to the carbonation includes testing a sample of the cement composition to determine volumetric expansion of the sample of the cement composition.

Statement 4. The method of any of the preceding statements, further comprising selecting a second cement composition and predicting a depth of carbonation in a second cement sheath formed from the second cement composition; predicting spatially varying mechanical properties of the second cement composition due to the carbonation; and determining a mechanical response of the second cement sheath after the carbonation based on the spatially varying mechanical properties of the second cement composition.

Statement 5. The method of any of the preceding statements, wherein the step of predicting spatially varying mechanical properties due to the carbonation includes testing a sample of the cement with s waves.

Statement 6. The method of any of the preceding statements, wherein the depth of carbonation is a function of at least permeability.

Statement 7. The method of any of the preceding statements, wherein the depth of carbonation is a function of at least a ratio of water to solids.

Statement 8. The method of any of the preceding statements, wherein the step of predicting spatially varying mechanical properties due to the carbonation includes performing a hardness test on a sample of the cement composition and relating indentation values from the hardness test to compressive and tensile strengths and Young's modulus.

Statement 9. The method of any of the preceding statements, wherein the step of predicting spatially varying mechanical properties due to the carbonation includes measuring porosity of a sample of the cement composition.

Statement 10. The method of any of the preceding statements, wherein the step of predicting spatially varying mechanical properties due to the carbonation includes testing a sample of the cement composition with p waves.

Statement 11. A method comprises predicting a depth of carbonation in a cement sheath formed from a cement composition; predicting spatially varying mechanical properties of the cement composition due to the carbonation; determining a mechanical response of the cement sheath based on the spatially varying mechanical properties of the cement composition; and selecting another cement composition based on the mechanical response of the cement sheath.

Statement 12. The method of any of the statement 11, further comprising preparing at least one cement composition based on the mechanical response of the cement sheath.

Statement 13. The method of any of the statements 11-12, wherein the step of predicting spatially varying mechanical properties due to the carbonation includes testing a sample of the cement composition to determine volumetric expansion.

Statement 14. The method of any of the statements 11-13, wherein the step of predicting spatially varying mechanical properties due to the carbonation includes testing a sample of the cement composition with s waves.

Statement 15. The method of any of the statements 11-14, wherein the step of predicting spatially varying mechanical properties due to the carbonation includes testing a sample of the cement composition with p waves.

Statement 16. The method of any of the statements 11-15, wherein the depth of carbonation is a function of at least permeability.

Statement 17. The method of any of the statements 11-16, wherein the depth of carbonation is a function of at least a ratio of water to solids.

Statement 18. The method of any of the statements 11-17, wherein the step of predicting spatially varying mechanical properties due to the carbonation includes performing a hardness test on a sample of the cement composition.

Statement 19. The method of any of the statements 11-18, wherein the step of predicting spatially varying mechanical properties due to the carbonation includes relating indentation values from the hardness test to compressive and tensile strengths and Young's modulus.

Statement 20. The method of any of the statements 11-19, wherein the step of predicting spatially varying mechanical properties due to the carbonation includes measuring porosity of a sample of the cement composition.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

For the sake of brevity, only certain ranges are explicitly disclosed herein. However, ranges from any lower limit may be combined with any upper limit to recite a range not explicitly recited as well as ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, as the present embodiments may be modified and practiced in different but equivalent manners. Although individual embodiments are discussed, all combinations of each embodiment are contemplated and covered by the disclosure. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method comprising:
predicting a depth of carbonation in a cement sheath formed from a cement composition placed in a wellbore, using a depth of carbonation model run on a computer;
predicting spatially varying mechanical properties of the cement composition due to the carbonation, using a mechanical property model run on the computer;
determining a mechanical response of the cement sheath based on the spatially varying mechanical properties of the cement composition, using a wellbore integrity analysis run on the computer;
preparing the cement composition based on the mechanical response of the cement sheath; and
introducing the cement composition into the wellbore.

2. The method of claim 1, wherein the step of predicting spatially varying mechanical properties due to the carbonation includes testing a sample of the cement composition to determine volumetric expansion.

3. The method of claim 1, further comprising:
selecting a second cement composition and predicting a depth of carbonation in a second cement sheath formed from the second cement composition;
predicting spatially varying mechanical properties of the second cement composition due to the carbonation; and
determining a mechanical response of the second cement sheath after the carbonation based on the spatially varying mechanical properties of the second cement composition.

4. The method of claim 1, wherein the step of predicting spatially varying mechanical properties due to the carbonation includes testing a sample of the cement composition with s waves.

5. The method of claim 1, wherein the depth of carbonation is a function of at least permeability.

6. The method of claim 1, wherein the depth of carbonation is a function of at least a ratio of water to solids.

7. The method of claim 1, wherein the step of predicting spatially varying mechanical properties due to the carbonation includes performing a hardness test on a sample of the cement composition and relating indentation values from the hardness test to compressive and tensile strengths and Young's modulus.

8. The method of claim 1, wherein the step of predicting spatially varying mechanical properties due to the carbonation includes measuring porosity of a sample of the cement composition.

9. The method of claim 1, wherein the step of predicting spatially varying mechanical properties due to the carbonation includes testing a sample of the cement composition with p waves.

10. A method comprising:
predicting a depth of carbonation in a cement sheath formed from a cement composition placed in a wellbore, using a depth of carbonation model run on a computer;
predicting spatially varying mechanical properties of the cement composition due to the carbonation, using a mechanical property model run on the computer;
determining a mechanical response of the cement sheath based on the spatially varying mechanical properties of the cement composition, using a wellbore integrity analysis run on the computer;
selecting a second cement composition based on the mechanical response of the cement sheath;
preparing the second cement composition based on the mechanical response of the cement sheath; and
introducing the second cement composition into the wellbore.

11. The method of claim 10, wherein the step of predicting spatially varying mechanical properties due to the carbonation includes testing a sample of the cement composition to determine volumetric expansion.

12. The method of claim 10, wherein the step of predicting spatially varying mechanical properties due to the carbonation includes testing a sample of the cement composition with s waves.

13. The method of claim 10, wherein the step of predicting spatially varying mechanical properties due to the carbonation includes testing a sample of the cement composition with p waves.

14. The method of claim 10, wherein the depth of carbonation is a function of at least permeability.

15. The method of claim 10, wherein the depth of carbonation is a function of at least a ratio of water to solids.

16. The method of claim 10, wherein the step of predicting spatially varying mechanical properties due to the carbonation includes performing a hardness test on a sample of the cement composition.

17. The method of claim 16, wherein the step of predicting spatially varying mechanical properties due to the carbonation further includes relating indentation values from the hardness test to compressive and tensile strengths and Young's modulus.

18. The method of claim 10, wherein the step of predicting spatially varying mechanical properties due to the carbonation includes measuring porosity of a sample of the cement composition.

* * * * *